(12) United States Patent
Zhang et al.

(10) Patent No.: US 10,517,545 B2
(45) Date of Patent: Dec. 31, 2019

(54) CT IMAGING APPARATUS AND METHOD, AND X-RAY TRANSCEIVING COMPONENT FOR CT IMAGING APPARATUS

(71) Applicant: General Electric Company, Schenectady, NY (US)

(72) Inventors: Xiaoyan Zhang, Beijing (CN); Xuyong Yang, Beijing (CN); Jun Guo, Beijing (CN)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 221 days.

(21) Appl. No.: 15/471,313

(22) Filed: Mar. 28, 2017

(65) Prior Publication Data

US 2017/0287173 A1    Oct. 5, 2017

(30) Foreign Application Priority Data

Mar. 31, 2016    (CN) .......................... 2016 1 0200106

(51) Int. Cl.
*A61B 6/00*    (2006.01)
*A61B 6/03*    (2006.01)
(Continued)

(52) U.S. Cl.
CPC ................ *A61B 6/035* (2013.01); *A61B 6/02* (2013.01); *A61B 6/022* (2013.01); *A61B 6/032* (2013.01);
(Continued)

(58) Field of Classification Search
CPC ......... A61B 6/032; A61B 6/035; A61B 6/037; A61B 6/06; A61B 6/4014; A61B 6/4064;
(Continued)

(56) References Cited

U.S. PATENT DOCUMENTS 5,668,851 A * 9/1997 Dobbs .................. G01T 1/1648
378/154
5,757,878 A * 5/1998 Dobbs .................... A61B 6/032
378/19

(Continued)

FOREIGN PATENT DOCUMENTS

JP         2009-056305 A      3/2009

*Primary Examiner* — Allen C. Ho
(74) *Attorney, Agent, or Firm* — Fletcher Yoder, P.C.

(57) ABSTRACT

The present invention provides an X-ray transceiving component for a CT imaging apparatus, comprising one or more bulb devices and a plurality of detector devices. The one or more bulb devices are configured to emit quadrate-tapered or fan-shaped X-ray beams. The plurality of detector devices are configure to receive the quadrate-tapered or fan-shaped X-ray beams emitted by the one or more bulb devices, each of the quadrate-tapered or fan-shaped X-ray beams comprising X-rays passing through a scanning field of view. Note that the plurality of detector devices are configured to receive X-rays passing through different areas within the scanning field of view, the one or more bulb devices are micro-focus bulb devices, and the plurality of detector devices are flat panel detectors or photoelectric coupling detectors. The present invention can greatly improve a resolution of CT imaging, increase imaging efficiency, and realize low-dose diagnosis in the case of ensuring that the scanning field of view is sufficient.

8 Claims, 14 Drawing Sheets

(51) Int. Cl.
  *A61B 6/02* (2006.01)
  *A61B 6/06* (2006.01)
  *G01V 5/00* (2006.01)
  *G01N 23/046* (2018.01)
  *G06T 7/00* (2017.01)
  *G06T 11/00* (2006.01)

(52) U.S. Cl.
  CPC ............... *A61B 6/037* (2013.01); *A61B 6/06* (2013.01); *A61B 6/40* (2013.01); *A61B 6/4007* (2013.01); *A61B 6/4014* (2013.01); *A61B 6/4064* (2013.01); *A61B 6/4078* (2013.01); *A61B 6/4085* (2013.01); *A61B 6/42* (2013.01); *A61B 6/4208* (2013.01); *A61B 6/4233* (2013.01); *A61B 6/44* (2013.01); *A61B 6/4429* (2013.01); *A61B 6/4435* (2013.01); *A61B 6/4441* (2013.01); *A61B 6/4447* (2013.01); *A61B 6/481* (2013.01); *A61B 6/52* (2013.01); *A61B 6/5235* (2013.01); *G01N 23/046* (2013.01); *G01V 5/005* (2013.01); *G01V 5/0016* (2013.01); *G01V 5/0058* (2013.01); *G06T 7/0012* (2013.01); *G06T 11/003* (2013.01)

(58) Field of Classification Search
  CPC ... A61B 6/4078; A61B 6/4085; A61B 6/4208; A61B 6/4233; A61B 6/4266; A61B 6/481; A61B 6/52; A61B 6/5205; A61B 6/02; A61B 6/022; A61B 6/40; A61B 6/4007; A61B 6/42; A61B 6/44; A61B 6/4429; A61B 6/4435; A61B 6/4441; A61B 6/4447; G01N 23/046; G01V 5/0016; G01V 5/005; G01V 5/0058
  USPC .................. 378/9, 19, 57, 41, 42, 196, 197
  See application file for complete search history.

(56) References Cited

U.S. PATENT DOCUMENTS

| | | | | |
|---|---|---|---|---|
| 5,781,606 | A * | 7/1998 | Dobbs | A61B 6/032 378/19 |
| 5,872,364 | A * | 2/1999 | Strömmer | A61B 6/14 250/370.09 |
| 5,912,938 | A * | 6/1999 | Dobbs | G01N 23/046 378/19 |
| 6,088,423 | A * | 7/2000 | Krug | G01V 5/0041 378/4 |
| 6,104,776 | A * | 8/2000 | Oikawa | G01N 23/20025 378/10 |
| 6,359,961 | B1 * | 3/2002 | Aufrichtig | A61B 6/022 378/41 |
| 6,473,487 | B1 * | 10/2002 | Le | G01N 23/04 378/57 |
| 6,483,892 | B1 * | 11/2002 | Wang | A61B 6/032 378/43 |
| 6,580,778 | B2 * | 6/2003 | Meder | G01V 5/0016 378/57 |
| 6,597,760 | B2 * | 7/2003 | Beneke | G01V 5/0016 378/57 |
| 6,763,083 | B2 * | 7/2004 | Fernandez | G01V 5/0058 378/196 |
| 6,856,667 | B2 * | 2/2005 | Ellengogen | G01V 5/0025 378/189 |
| 6,914,959 | B2 * | 7/2005 | Bailey | A61B 6/022 378/41 |
| 6,975,699 | B2 * | 12/2005 | Kresse | G01V 5/0016 378/19 |
| 7,020,241 | B2 * | 3/2006 | Beneke | G01V 5/0016 378/54 |
| 7,027,554 | B2 * | 4/2006 | Gaultier | G01T 1/2985 378/19 |
| 7,035,371 | B2 * | 4/2006 | Boese | A61B 6/022 378/41 |
| 7,039,154 | B1 * | 5/2006 | Ellenbogen | A61B 6/482 378/19 |
| 7,103,137 | B2 * | 9/2006 | Seppi | G01N 23/04 378/57 |
| 7,106,825 | B2 * | 9/2006 | Gregerson | G06T 11/005 378/19 |
| 7,108,421 | B2 * | 9/2006 | Gregerson | A61B 6/032 378/197 |
| 7,164,747 | B2 * | 1/2007 | Ellenbogen | G01N 23/046 378/19 |
| 7,209,538 | B2 * | 4/2007 | Sukovic | A61B 6/022 378/189 |
| 7,227,924 | B2 * | 6/2007 | Zhou | A61B 6/032 378/10 |
| 7,227,925 | B1 * | 6/2007 | Mansfield | A61N 5/1049 378/41 |
| 7,233,644 | B1 * | 6/2007 | Bendahan | G01N 23/046 378/57 |
| 7,298,814 | B2 * | 11/2007 | Popescu | A61B 6/032 378/19 |
| 7,302,033 | B2 * | 11/2007 | Carrano | A61B 6/022 378/41 |
| 7,319,737 | B2 * | 1/2008 | Singh | G01N 23/046 378/57 |
| 7,372,937 | B2 * | 5/2008 | Wang | G01N 23/046 378/16 |
| 7,400,701 | B1 * | 7/2008 | Cason | G01V 5/0025 378/57 |
| 7,440,544 | B2 * | 10/2008 | Scheinman | G01N 23/046 378/4 |
| 7,453,977 | B2 * | 11/2008 | DiBianca | A61B 6/032 257/E27.14 |
| 7,453,978 | B1 * | 11/2008 | DiBianca | A61B 6/4233 378/19 |
| 7,526,064 | B2 * | 4/2009 | Akery | G01N 23/04 378/198 |
| 7,545,905 | B2 * | 6/2009 | Münker | G01N 23/046 378/20 |
| 7,606,348 | B2 * | 10/2009 | Foland | G01N 23/046 378/4 |
| 7,620,144 | B2 * | 11/2009 | Bodduluri | A61B 6/02 378/41 |
| 7,806,589 | B2 * | 10/2010 | Tashman | A61B 5/1038 378/193 |
| 7,809,102 | B2 * | 10/2010 | Brada | A61B 6/022 378/20 |
| 7,826,585 | B2 * | 11/2010 | Proksa | A61B 6/032 378/5 |
| 7,831,012 | B2 * | 11/2010 | Foland | G01N 23/04 378/57 |
| 7,840,249 | B2 * | 11/2010 | Wang | A61B 6/032 378/4 |
| 7,933,378 | B2 * | 4/2011 | Proksa | A61B 6/032 378/9 |
| 7,949,089 | B2 * | 5/2011 | Dafni | A61B 6/022 378/6 |
| 8,180,017 | B2 * | 5/2012 | Forthmann | A61B 6/032 378/156 |
| 8,218,716 | B2 * | 7/2012 | Handa | A61B 6/022 378/4 |
| 8,300,762 | B2 * | 10/2012 | Suzuki | A61B 6/032 378/15 |
| 8,300,766 | B2 * | 10/2012 | Handa | A61B 6/022 378/207 |
| 8,340,245 | B2 * | 12/2012 | Herranz | G01N 23/04 378/4 |
| 8,439,565 | B2 * | 5/2013 | Mastronardi | G01N 23/04 378/205 |
| 8,442,184 | B2 * | 5/2013 | Forthmann | A61B 6/032 378/5 |
| 8,498,377 | B2 * | 7/2013 | Fadler | A61B 6/032 378/62 |

(56) References Cited

U.S. PATENT DOCUMENTS

| | | | | |
|---|---|---|---|---|
| 8,768,032 B2* | 7/2014 | Basu | ............... | G06T 11/005 |
| | | | | 250/559.05 |
| 8,891,726 B2* | 11/2014 | Wieczorek | ............ | A61B 6/032 |
| | | | | 378/9 |
| 8,908,826 B2* | 12/2014 | Bernhardt | .............. | A61B 6/022 |
| | | | | 378/42 |
| 8,971,487 B2* | 3/2015 | Mastronardi | ........ | G01V 5/0008 |
| | | | | 378/57 |
| 9,036,777 B2* | 5/2015 | Ohishi | .................. | A61B 6/022 |
| | | | | 378/41 |
| 9,277,893 B2* | 3/2016 | Tsukagoshi | ............ | A61B 6/022 |
| 9,417,340 B2* | 8/2016 | Basu | ..................... | G01T 1/2985 |
| 9,427,201 B2* | 8/2016 | West | ..................... | A61B 6/466 |
| 9,579,071 B2* | 2/2017 | Lee | ........................ | A61B 6/022 |
| 9,864,091 B2* | 1/2018 | Chen | ..................... | G01V 5/005 |
| 10,278,654 B2* | 5/2019 | Sadakane | ............... | A61B 6/025 |
| 2010/0322498 A1 | 12/2010 | Wieczorek et al. | | |

\* cited by examiner

CT IMAGING APPARATUS AND METHOD, AND X-RAY TRANSCEIVING COMPONENT FOR CT IMAGING APPARATUS

FIELD

The present invention relates to the field of X-ray imaging, particularly to a CT imaging apparatus and method, and an X-ray transceiving component for the CT imaging apparatus.

BACKGROUND

A spatial resolution and a scanning field of view are important parameters in the computed tomography (CT) medical imaging technology, in which the scanning field of view affects a size of an imaging range and the spatial resolution affects imaging definition. Currently, macro CT imaging apparatuses mostly employ a bulb with a larger focal spot and fan-shaped beams to scan, in which the scanning field of view can reach about 500 millimeters, but relatively, the spatial resolution is lower and can only reach about 0.2-0.5 millimeters.

Although a dental CT imaging apparatus or a micro CT imaging apparatus has a higher spatial resolution, its scanning field of view is very limited. For example, a scanning field of view of the dental CT imaging apparatus is about 200 millimeters and a scanning field of view of the micro CT imaging apparatus is about 50 millimeters.

Therefore, there is a need to provide a CT imaging apparatus and method that can improve the spatial resolution while maintaining the advantage of the scanning field of view, such that more accurate results of disease diagnosis can be obtained.

SUMMARY

One objective of the present invention is to provide a CT imaging apparatus and method that can improve a spatial resolution while maintaining an advantage of a scanning field of view, and an X-ray transceiving component for the CT imaging apparatus.

An exemplary embodiment of the present invention provides an X-ray transceiving component for a CT imaging apparatus, comprising one or more bulb devices and a plurality of detector devices. The one or more bulb devices are configured to emit quadrate-tapered or fan-shaped X-ray beams. The plurality of detector devices are configure to receive the quadrate-tapered or fan-shaped X-ray beams emitted by the one or more bulb devices, each of the quadrate-tapered or fan-shaped X-ray beams comprising X-rays passing through a scanning field of view. Note that the plurality of detector devices are configured to receive X-rays passing through different areas within the scanning field of view, the one or more bulb devices are micro-focus bulb devices, and the plurality of detector devices are flat panel detectors or photoelectric coupling detectors.

An exemplary embodiment of the present invention also provides a CT imaging apparatus, comprising a rack and further comprising one or more X-ray transceiving components for the CT imaging apparatus as described above, the X-ray transceiving components being installed on the rack.

An exemplary embodiment of the present invention also provides a CT imaging method, comprising the steps of:
determining a resolution of an image needing to be formed according to a diagnosis type;
controlling a CT imaging apparatus to perform imaging scan, comprising: controlling all or part of a plurality of bulb devices of the CT imaging apparatus to emit quadrate-tapered or fan-shaped X-ray beams to a scanned object according to the above diagnosis type, the CT imaging apparatus further comprising a plurality of detector devices, the plurality of detector devices corresponding to the plurality of bulb devices and being configured to receive the quadrate-tapered or fan-shaped X-ray beams emitted by the corresponding bulb devices, each quadrate-shaped or fan-shaped X-ray beam comprising X-rays passing through a scanning field of view, wherein the plurality of detector devices are configured to receive X-rays passing through different areas within the scanning field of view, the above plurality of bulb devices are micro-focus bulb devices, and the above plurality of detector devices are flat panel detectors or photoelectric coupling detectors;
collecting image data from detector devices corresponding to all or part of the above plurality of bulb devices and storing the image data; and
determining an image reconstruction mode according to the determined resolution and reconstructing the image in the determined image reconstruction mode, the image reconstruction mode comprising a first image reconstruction mode and a second image reconstruction mode; the first image reconstruction mode comprising: dividing the stored image data into data blocks and reconstructing the image according to the data blocks, each data block comprising data obtained by fusing data of a plurality of pixel points; the second image reconstruction mode comprising: reconstructing the image according to data of all pixel points in the stored image data.

The embodiments of the present invention emit quadrate-tapered or fan-shaped X-ray beams passing through a scanning field of view by one or more bulb devices and employ a plurality of detector devices to receive X-rays passing through different areas within the scanning field of view. Even if the one or more bulb devices have a smaller focus, a larger scanning field of view can still be formed such that a higher spatial resolution is provided, image quality is improved, and an application range is expanded while the scanning field of view is not sacrificed.

Moreover, since a higher spatial resolution can be achieved, determining the resolution according to the diagnosis type and utilizing the corresponding image reconstruction mode according to different resolution requirements to obtain an image of the corresponding quality can be realized, which improves imaging efficiency such that a pathological change can be diagnosed earlier and an image of a lesion area can be obtained by selecting an image reconstruction mode, and thereby repetition of ray scanning on a patient is avoided and low-dose diagnosis is realized.

Other features and aspects will be apparent through the following detailed description, figures and claims.

BRIEF DESCRIPTION OF THE DRAWINGS

The present invention can be understood better in light of the description of exemplary embodiments of the present invention with reference to the accompanying drawings, in which.

DETAILED DESCRIPTION

Figure 1:
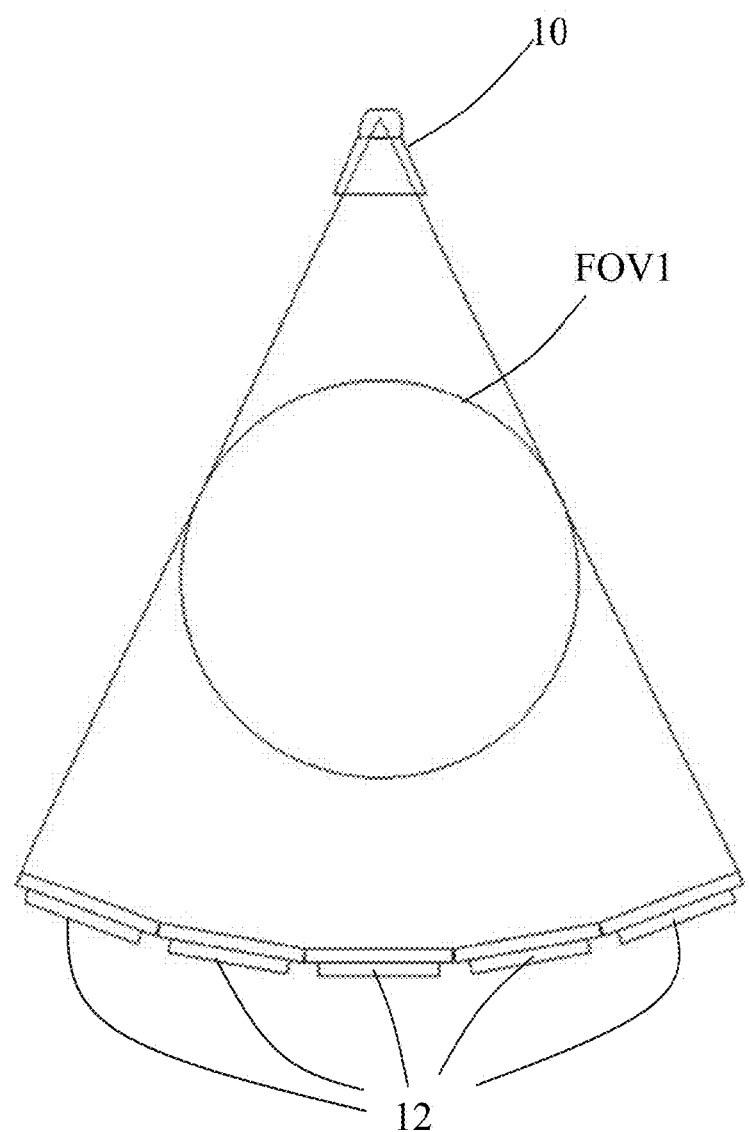
FIG. 1, FIG. 2 and FIG. 3 are structural schematic diagrams of an X-ray transceiving component for a CT imaging apparatus provided by a first embodiment of the present invention, respectively.

Hereafter, a detailed description will be given for preferred embodiments of the present disclosure. It should be pointed out that in the detailed description of the embodiments, for simplicity and conciseness, it is impossible for the Description to describe all the features of the practical embodiments in details. It should be understood that in the process of a practical implementation of any embodiment, just as in the process of an engineering project or a designing project, in order to achieve a specific goal of the developer and in order to satisfy some system-related or business-related constraints, a variety of decisions will usually be made, which will also be varied from one embodiment to another. In addition, it can also be understood that although the effort made in such developing process may be complex and time-consuming, some variations such as design, manufacture and production on the basis of the technical contents disclosed in the disclosure are just customary technical devices in the art for those of ordinary skilled in the art associated with the contents disclosed in the present disclosure, which should not be regarded as insufficient disclosure of the present disclosure.

Unless defined otherwise, all the technical or scientific terms used in the Claims and the Description should have the same meanings as commonly understood by one of ordinary skilled in the art to which the present disclosure belongs. The terms "first", "second" and the like in the Description and the Claims of the present utility model do not mean any sequential order, number or importance, but are only used for distinguishing different components. The terms "a", "an" and the like do not denote a limitation of quantity, but denote the existence of at least one. The terms "comprises", "comprising", "includes", "including" and the like mean that the element or object in front of the "comprises", "comprising", "includes" and "including" covers the elements or objects and their equivalents illustrated following the "comprises", "comprising", "includes" and "including", but do not exclude other elements or objects. The term "coupled" or "connected" or the like is not limited to being connected physically or mechanically, nor limited to being connected directly or indirectly.

An embodiment of the present invention provides an X-ray transceiving component for a CT imaging apparatus, including one or more bulb devices and a plurality of detector devices. Each bulb device is configured to emit quadrate-tapered or fan-shaped X-ray beams. For example, by a collimator with a diaphragm of a corresponding shape provided in the bulb device, the bulb device may emit the quadrate-tapered or fan-shaped X-ray beams. Different from the traditional fan-shaped X-ray beam, the quadrate-tapered or fan-shaped X-ray beam has a larger width in a radial direction.

Each quadrate-tapered or fan-shaped X-ray beam includes X-rays passing through a scanning field of view, wherein the above plurality of detector devices are configured to receive X-rays passing through different areas within the scanning field of view. For example, when the number of the bulb devices is one, a plurality of detector devices may be arranged to receive a part of the quadrate-tapered or fan-shaped X-ray beams emitted by the one bulb device respectively; when the number of the bulb devices are more than one, a plurality of detectors may be arranged and each detector is made receive the quadrate-tapered or fan-shaped X-ray beams emitted by one corresponding bulb device.

The above one or more bulb devices may be micro-focus bulb devices, and the above plurality of detector devices may be flat panel detectors or photoelectric coupling detectors. Employing the micro-focus bulb devices or the flat panel detectors or the photoelectric coupling detectors is helpful in obtaining a higher spatial resolution.

Figure 2:
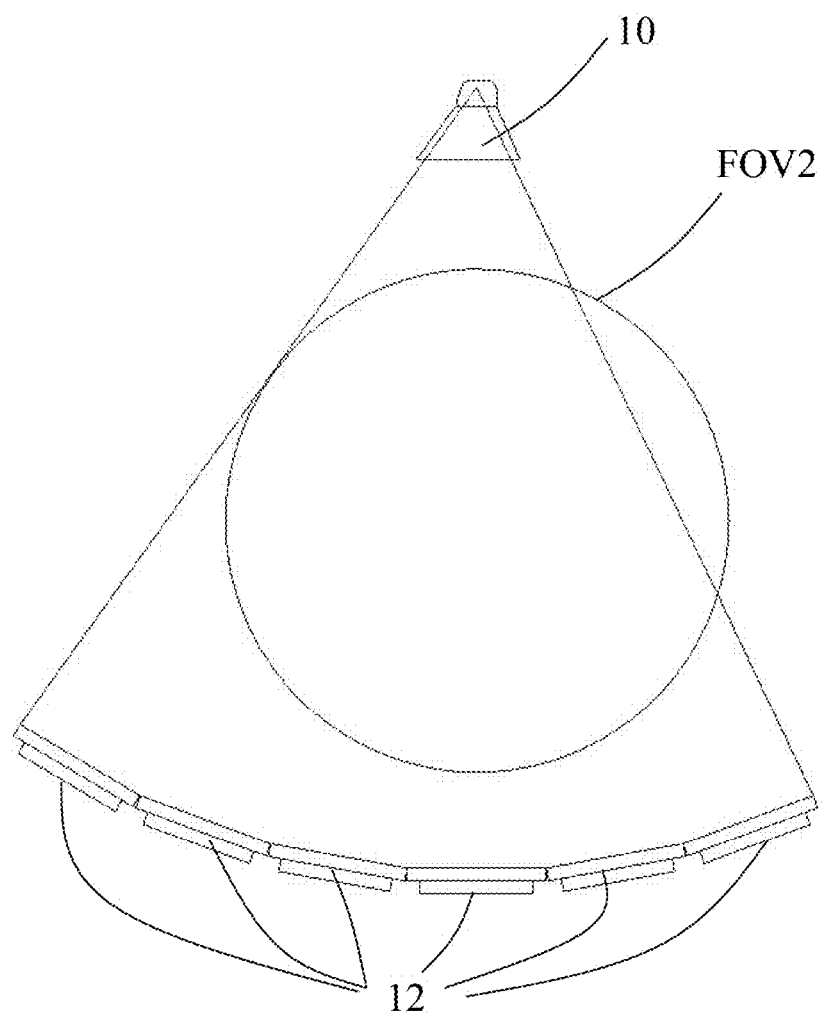
Figure 3:
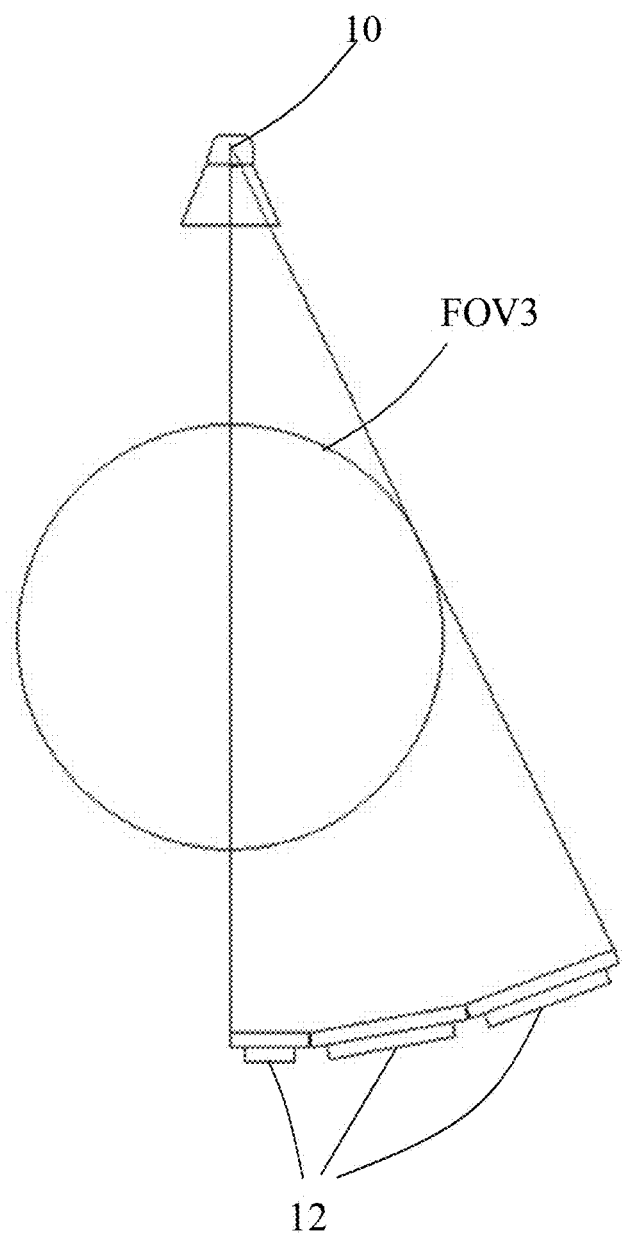

FIG. 1, FIG. 2 and FIG. 3 are structural schematic diagrams of an X-ray transceiving component for a CT imaging apparatus provided by a first embodiment of the present invention, respectively. As shown in FIG. 1, FIG. 2 and FIG. 3, in the first embodiment, the above one or more bulb devices include a first bulb device 10, and the above plurality of detector devices include a plurality of detector devices 12. Each detector device 12 is configured to receive a part of quadrate-tapered or fan-shaped X-ray beams emitted by the first bulb device 10.

In the first embodiment, a plurality of detector devices 12 are provided to receive the quadrate-tapered or fan-shaped X-ray beams emitted by the first bulb device 10.

Optionally, as shown in FIG. 1, the quadrate-tapered or fan-shaped X-ray beams emitted by the first bulb device 10 may cover the whole scanning field of view FOV1. At this point, a center of the quadrate-tapered or fan-shaped X-ray beams emitted by the first bulb device 10 coincides with a center of the scanning field of view FOV1. The above scanning field of view FOV1 may have a plurality of areas a1, each of which is a transmission path of the X-ray beam received by one corresponding detector device 12. Therefore, the plurality of detector devices 12 are configured to receive X-rays passing through different areas a1 within the scanning field of view, and imaging scan in the whole scanning field of view FOV1 may be realized.

Optionally, as shown in FIG. 2 and FIG. 3, the quadrate-tapered or fan-shaped X-ray beams emitted by the first bulb device 10 may also cover a part of the whole scanning field of view FOV2 or FOV3 only. At this point, in FIG. 2, a center of the quadrate-tapered or fan-shaped X-ray beams emitted by the first bulb device 10 deviates from a center of the scanning field of view FOV2, while in FIG. 3, a center of the quadrate-tapered or fan-shaped X-ray beams emitted by the first bulb device 10 deviates from a center of the scanning field of view FOV3. In this way, the same number of detector devices 12 or less detector devices 12 may be used to achieve a larger scanning field of view. In other words, the scanning field of view FOV2 in FIG. 2 or the scanning field of view FOV3 in FIG. 3 may be made larger than the scanning field of view FOV1 in FIG. 1.

Figure 4:
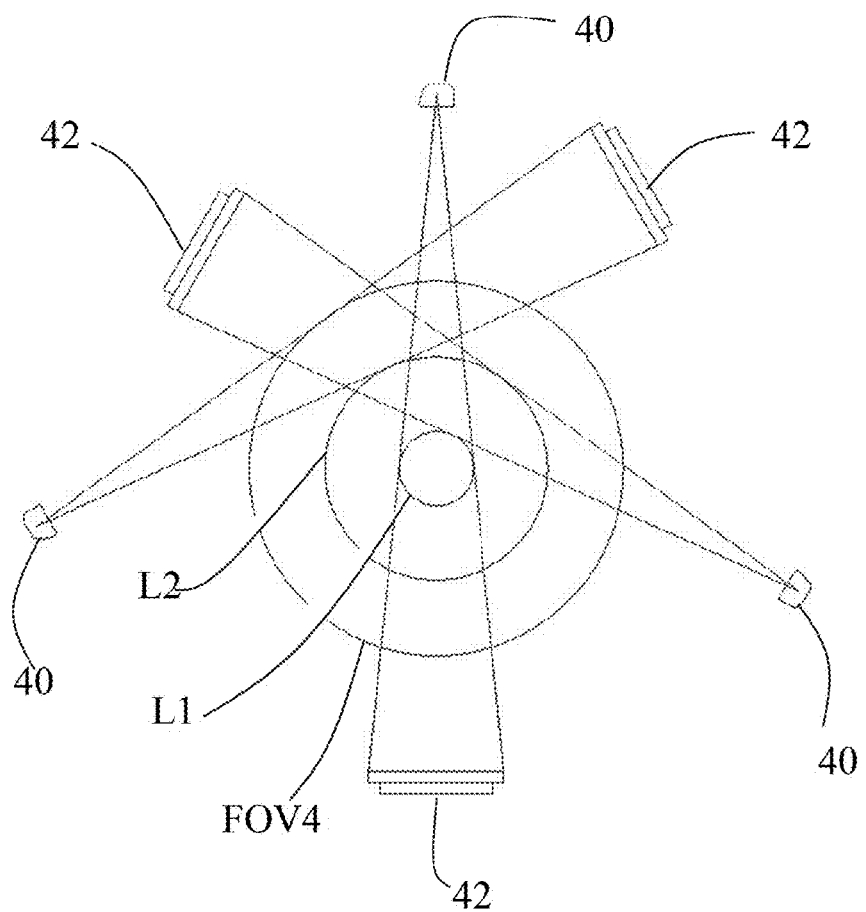
FIG. 4 is a structural schematic diagram of an X-ray transceiving component for a CT imaging apparatus provided by a second embodiment of the present invention.

FIG. 4 is a structural schematic diagram of an X-ray transceiving component for a CT imaging apparatus provided by a second embodiment of the present invention. As shown in FIG. 4, the X-ray transceiving component includes a plurality of second bulb devices 40 and a plurality of detector devices 42, in which the plurality of second bulb devices 40 correspond to the plurality of detector devices 42 respectively.

As shown in FIG. 4, in the second embodiment, the plurality of second bulb devices 40 and the plurality of detector devices 42 are arranged at intervals outside a scanning field of view FOV4, and each detector device 42 is provided between two second bulb devices 40.

Each detector device 42 is arranged opposite to the corresponding second bulb device 40, so as to be configured to receive the quadrate-tapered or fan-shaped X-ray beams emitted by the corresponding second bulb device 40.

In the above way, quadrate-tapered or fan-shaped X-ray beams emitted by the plurality of second bulb devices 40 pass through different areas of the scanning field of view FOV4 before being received by the corresponding detector devices 42.

Optionally, centers of the quadrate-tapered or fan-shaped X-ray beams emitted by the plurality of second bulb devices 40 may all coincide with a center of the above scanning field of view FOV4 to form a smaller scanning field of view, or a center of quadrate-tapered or fan-shaped X-ray beams emitted by at least one of the plurality of second bulb devices 40 deviates from the center of the scanning field of view FOV4 to form a larger scanning field of view. For example, in FIG. 4, by adjusting relative positions of three second bulb devices 40 and the corresponding detector devices 42, centers of quadrate-tapered or fan-shaped X-ray beams emitted by the three second bulb devices 40 may be made coincide with each other to form a smallest scanning field of view (a range as shown by a circle L1); or centers of quadrate-tapered or fan-shaped X-ray beams emitted by two second bulb devices 40 of the three may be made coincide with each other and deviate from a center of quadrate-tapered or fan-shaped X-ray beams emitted by a third second bulb device 40 to form a slightly larger scanning field of view (a range as shown by a circle L2); when the centers of the quadrate-tapered or fan-shaped X-ray beams emitted by the three second bulb devices 40 do not coincide, a larger scanning field of view, e.g., the scanning field of view FOV4 in FIG. 4, may be formed.

Of course, the number of the second bulb devices 40 and their corresponding detector devices 42 may also be increased appropriately to increase the scanning field of view, or the number of the second bulb devices 40 and their corresponding detector devices 42 may also be decreased appropriately to decrease the scanning field of view.

Figure 5:
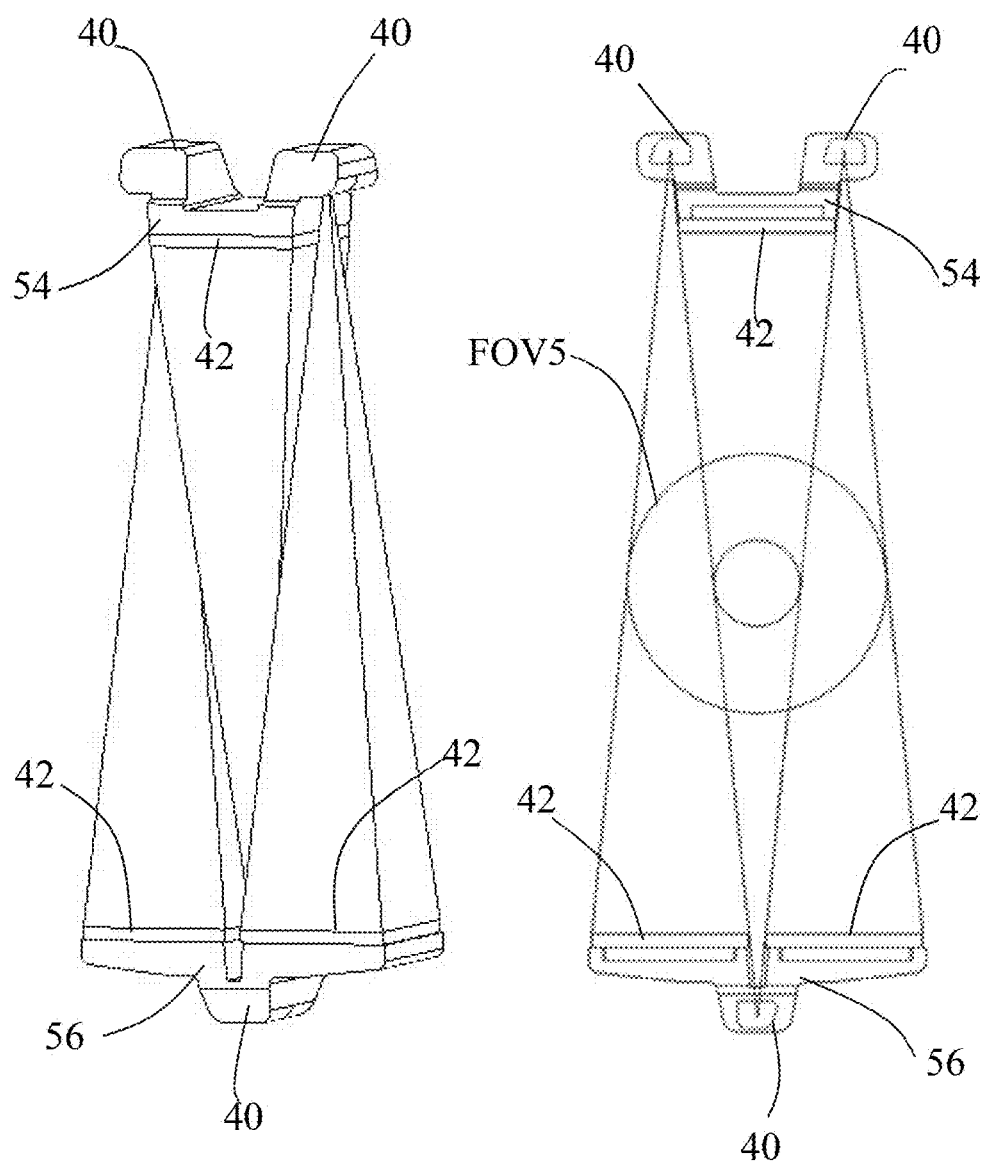
FIG. 5, FIG. 6 and FIG. 7 are structural schematic diagrams of an X-ray transceiving component for a CT imaging apparatus provided by a third embodiment of the present invention.
Figure 6:
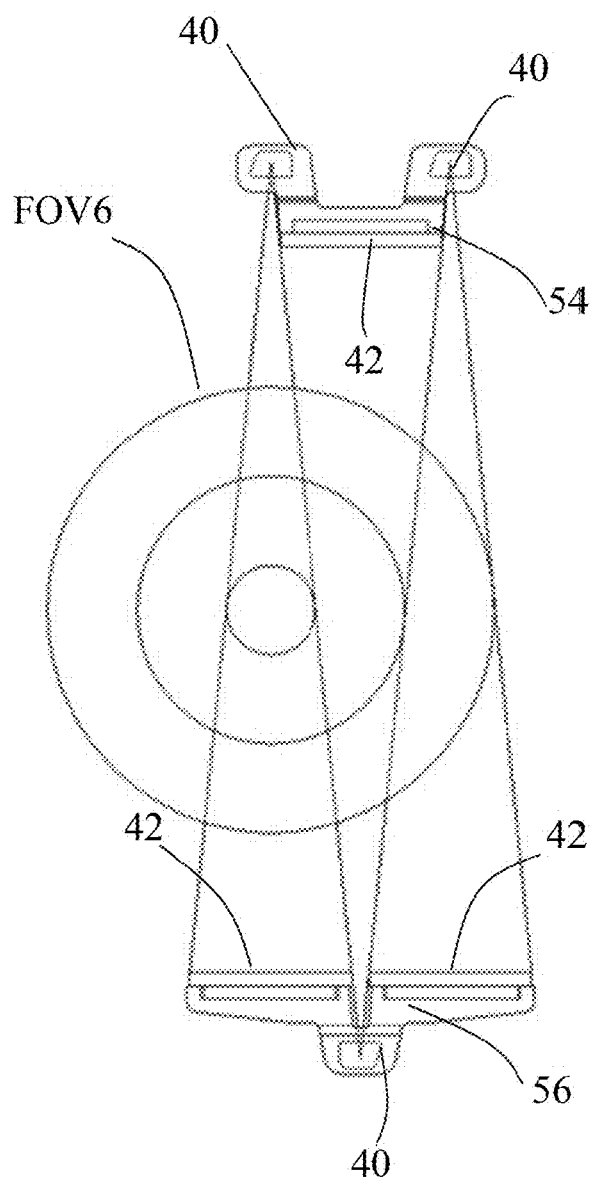
Figure 7:
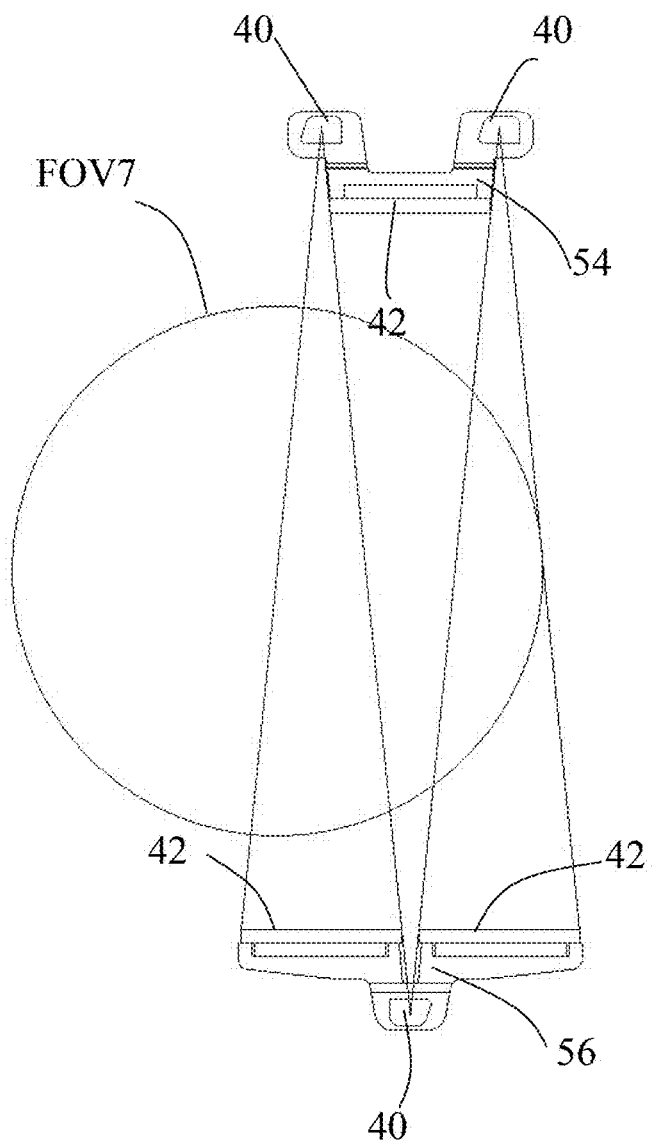
Figure 8:
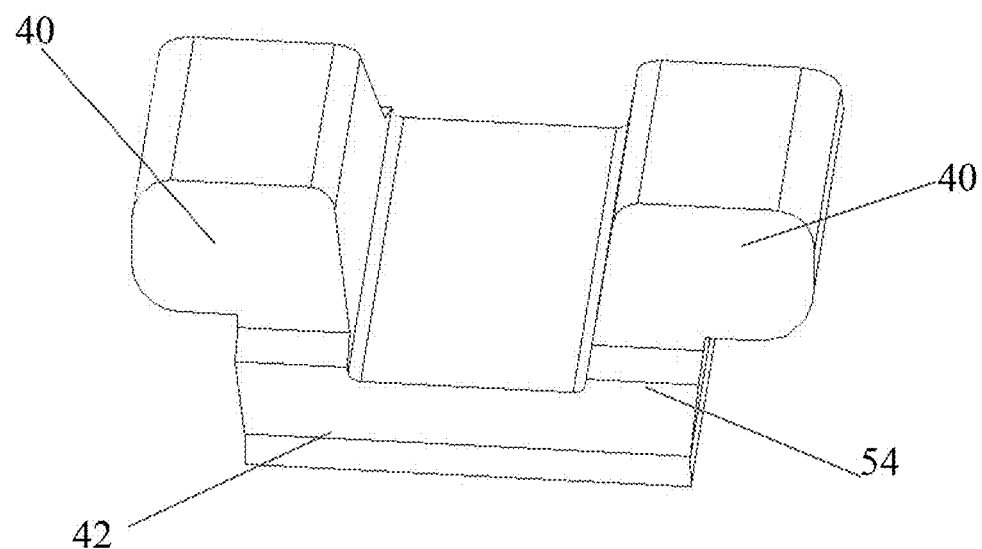
FIG. 8 is a structural schematic diagram of a first supporting member in FIG. 5 and second bulb devices and detector devices on the first supporting member.
Figure 9:
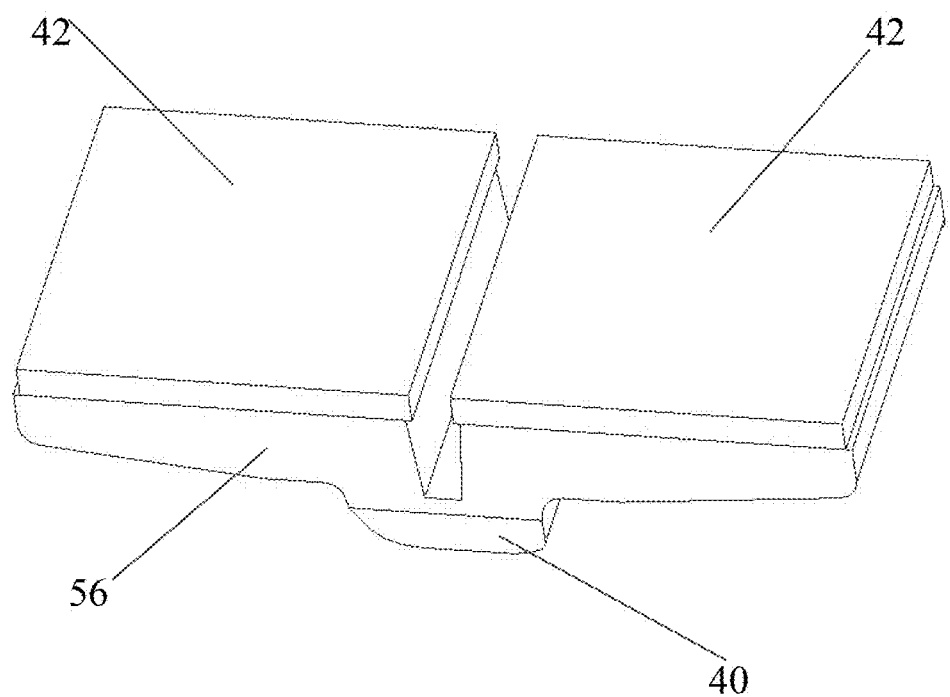
FIG. 9 is a structural schematic diagram of a second supporting member in FIG. 5 and second bulb devices and detector devices on the second supporting member.

FIG. 5, FIG. 6 and FIG. 7 are structural schematic diagrams of an X-ray transceiving component for a CT imaging apparatus provided by a third embodiment of the present invention. FIG. 8 is a structural schematic diagram of a first supporting member in FIG. 5 and second bulb devices and detector devices on the first supporting member. FIG. 9 is a structural schematic diagram of a second supporting member in FIG. 5 and second bulb devices and detector devices on the second supporting member. As shown in FIG. 5-FIG. 9, the X-ray transceiving component is similar to the X-ray transceiving component in the second embodiment (FIG. 4), also including a plurality of second bulb devices 40 and a plurality of detector devices 42 corresponding to the plurality of second bulb devices 40, the difference being that the X-ray transceiving component further includes a first supporting member 54 and a second supporting member 56.

The first supporting member 54 includes an upper supporting surface and a lower supporting surface. The second supporting member 56 also includes an upper supporting surface and a lower supporting surface.

One second bulb device 40 is provided on the lower supporting surface of the second supporting member 56, one detector device 42 is provided on the lower supporting surface of the first supporting member 54, and the detector device 42 provided on the lower supporting surface of the first supporting member 54 is opposite to the second bulb device 40 provided on the lower supporting surface of the second supporting member 56 so as to be capable of receiving quadrate-tapered or fan-shaped X-ray beams emitted by the second bulb device 40.

Two second bulb devices 40 are separately provided at two sides of the upper supporting surface of the first supporting member 54, two detector devices 42 are separately provided at two side of the upper supporting surface of the second supporting member 56, and the two detector devices 42 provided on the upper supporting surface of the second supporting member 56 are respectively opposite to the two second bulb devices 40 provided on the upper supporting surface of the first supporting member 54 so as to be capable of receiving quadrate-tapered or fan-shaped X-ray beams emitted by the two second bulb devices 40 respectively.

The two second bulb devices 40 provided on the upper supporting surface of the first supporting member 54 are symmetric with respect to a center of the detector device 42 provided on the lower supporting surface of the first supporting member 54. In other words, on the first supporting member 54, distances between the center of the detector device 42 and centers of the two second bulb devices 40 are equal.

Accordingly, the two detector devices 42 provided on the upper supporting surface of the second supporting member 56 are symmetric with respect to a center of the second bulb device 40 provided on the lower supporting surface of the second supporting member 56. In other words, on the second supporting member 56, distances between the center of the second bulb device 40 and centers of the two detector devices 42 are equal.

In the present embodiment, in order to allow the detector device 42 provided on the first supporting member 54 to receive quadrate-tapered or fan-shaped X-ray beams emitted by the second bulb device 40 provided on the second supporting member 56 and in order to allow the detector devices 42 provided on the second supporting member 56 to receive quadrate-tapered or fan-shaped X-ray beams emitted by the second bulb devices 40 provided on the first supporting member 54, an opening for light transmission path is arranged on both the first supporting member 54 and the second supporting member 56. For example, the opening of the first supporting member 54 is provided at two sides thereof and the opening of the second supporting member 56 is provided in the middle position thereof.

Optionally, as shown in FIG. 5, a center of the quadrate-tapered or fan-shaped X-ray beams emitted by the second bulb device 40 provided on the lower supporting surface of the second supporting member 56 coincides with a center of a scanning field of view. In other words, the center of the quadrate-tapered or fan-shaped X-ray beams emitted by the second bulb device 40 provided on the lower supporting surface of the second supporting member 56 serves as the center of the scanning field of view. At this point, a scanning field of view FOV5 as shown in FIG. 5 is formed.

Optionally, a center of the quadrate-tapered or fan-shaped X-ray beams emitted by the second bulb device 40 provided on the lower supporting surface of the second supporting member 56 may also be made deviate from the center of the scanning field of view. For example, in FIG. 6, the center of the quadrate-tapered or fan-shaped X-ray beams emitted by the second bulb devices 40 provided on the upper supporting surface of the first supporting member 54 serves as the center of the scanning field of view, and a scanning field of view FOV6 as shown in FIG. 6 may be formed, whose range is larger than that of the scanning field of view FOV5 in FIG. 5. For another example, in FIG. 7, when the X-ray beams emitted by the X-ray transceiving component only occupies an area that is half of the scanning field of view (at this point, a distance of the center of the quadrate-tapered or fan-shaped X-ray beams emitted by the second bulb device 40 provided on the lower supporting surface of the second supporting member 56 from the center of the scanning field of view is farther than that in FIG. 6), a scanning field of view FOV7 as shown in FIG. 7 may be formed, whose range is larger than that of the scanning field of view FOV6 in FIG. 6.

Figure 10A:
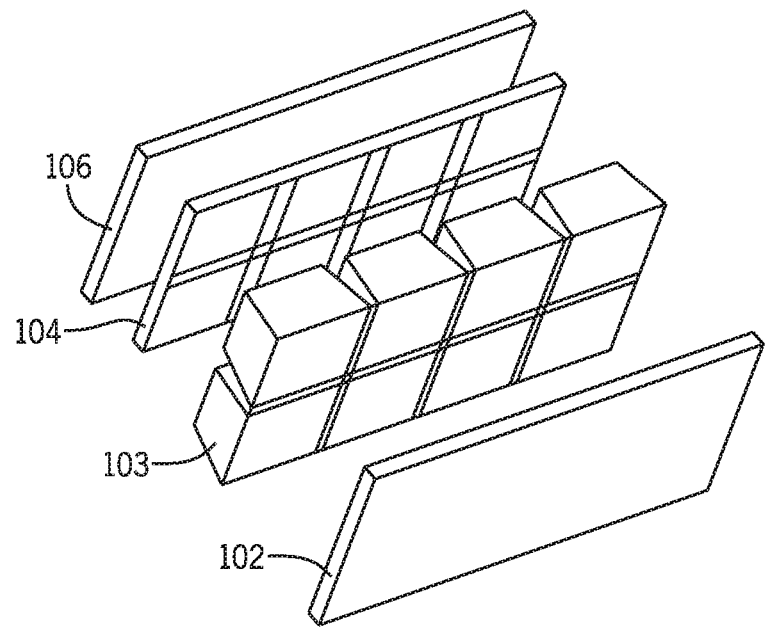
FIG. 10a is a structural schematic diagram of a detector device in FIG. 1-FIG. 9 when employing a photoelectric coupling detector, specifically a structural schematic diagram of a detector device in which a single scintillator corresponds to a plurality of photoelectric coupling devices.
Figure 10B:
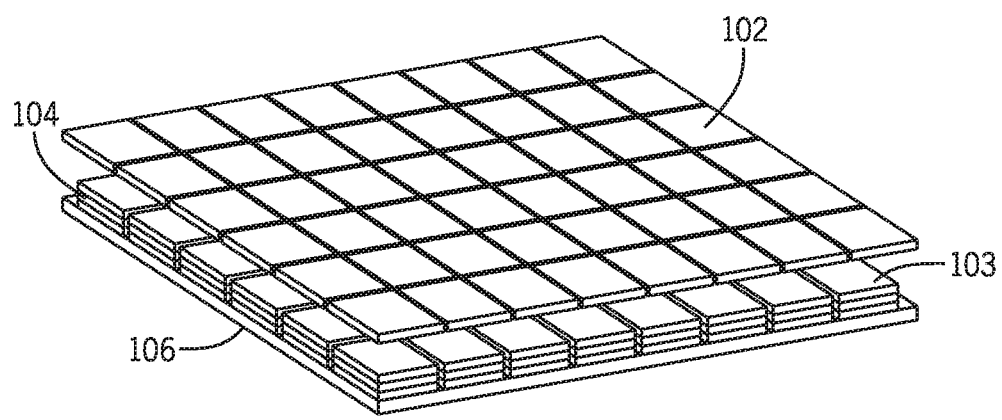
FIG. 10b is a structural schematic diagram of a detector device in FIG. 1-FIG. 9 when employing a photoelectric coupling detector, specifically a structural schematic diagram of a detector device in which a plurality of scintillators correspond to a plurality of photoelectric coupling devices one by one.
Figure 10C:
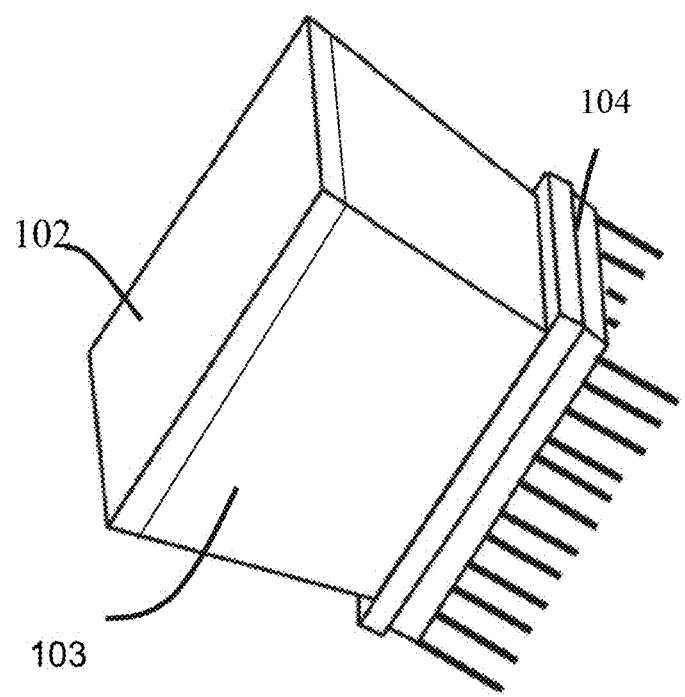
FIG. 10c is a schematic diagram of a photoelectric coupling device in FIG. 10b in combination with a lower bottom surface of a photoconductive device.

FIG. 10a is a structural schematic diagram of a detector device in FIG. 1-FIG. 9 when employing a photoelectric coupling detector, specifically a structural schematic diagram of the detector device in which a single scintillator corresponds to a plurality of photoelectric coupling devices; FIG. 10b is a structural schematic diagram of a detector device in FIG. 1-FIG. 9 when employing a photoelectric coupling detector, specifically a structural schematic diagram of the detector device in which a plurality of scintillators correspond to a plurality of photoelectric coupling devices one by one; FIG. 10c is a schematic diagram of a photoelectric coupling device in FIG. 10b in combination with a lower surface of a photoconductive device; as shown above, the above detector device may be a photoelectric coupling detector. As shown in FIG. 10a-FIG. 10c, the above photoelectric coupling detector includes a scintillator layer 102, a photoelectric coupling device array 104, and a circuit substrate 106 in combination with the photoelectric coupling device array 104. Since each of the charge photoelectric coupling devices in the photoelectric coupling device array 104 generally includes a circuit carrier and function pins, said function pins will extend to side ends of the circuit carrier and form gaps in rows or columns in the array. After the X-rays are converted into visible light through the scintillator layer 102, the visible light is transmitted onto the photoelectric coupling device array 104 for photoelectric conversion. At this point, the gaps formed due to the function pins will result in light loss or interference.

In an embodiment of the present invention, a photoconductive device array 103 corresponding to the photoelectric coupling device array 104 is further provided between the scintillator layer 102 and the photoelectric coupling device array 104, each photoconductive device in the photoconductive device array 103 is a quadrate-tapered light-fiber structure, an upper surface of each photoconductive device is combined with the scintillator layer 102, and a lower surface of each photoconductive device is combined with the corresponding photoelectric coupling device.

Since a cross-sectional area of a beam will gradually decrease during transmission of the beam, the embodiment of the present invention makes light loss during transmission of the beam from the scintillator layer 102 to the photoelectric coupling device smaller by arranging the photoconductive device and making the photoconductive device be a quadrate-tapered light-fiber structure, and interference will not be generated due to the gaps between the rows or columns of the photoelectric coupling device array 104, further improving an image resolution.

Figure 11:
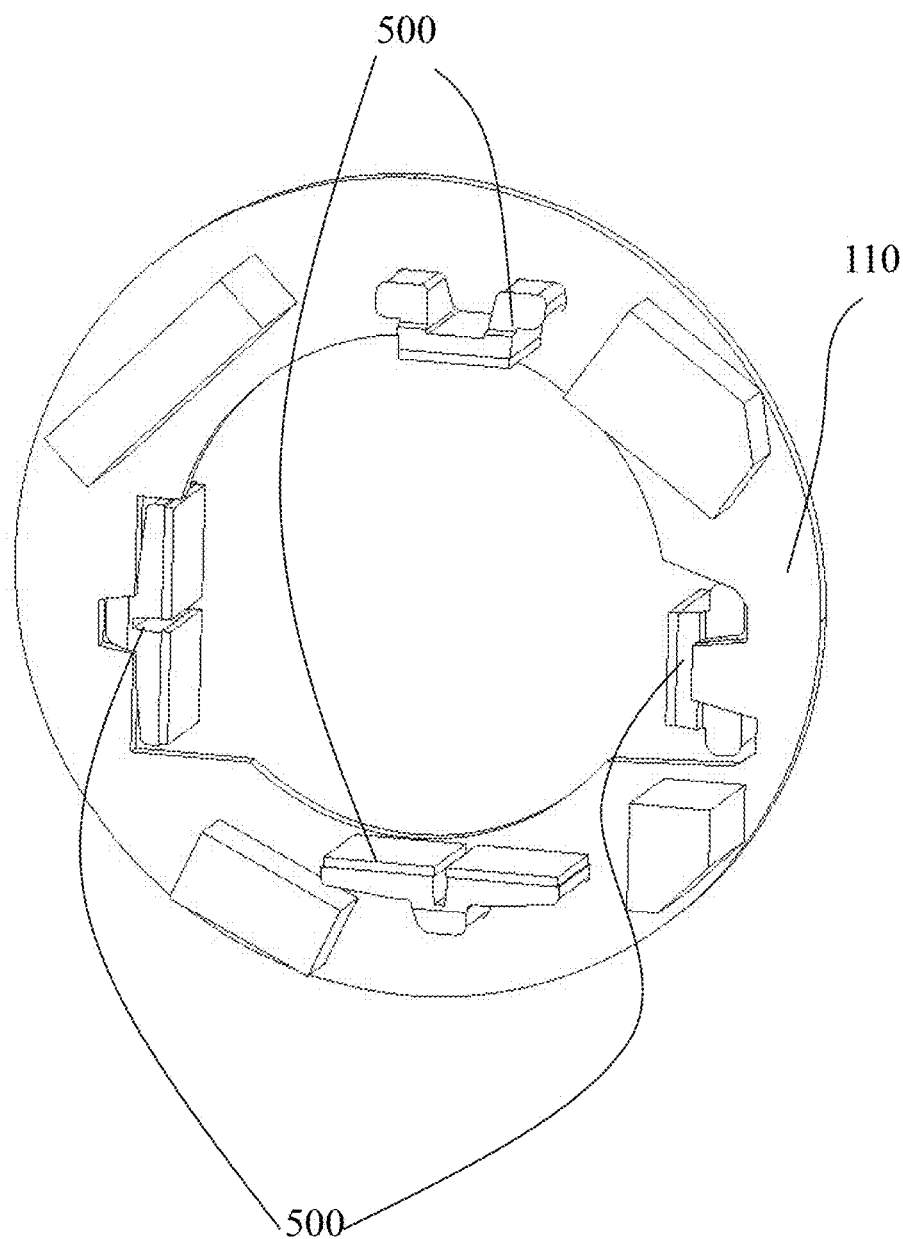
FIG. 11 is a structural schematic diagram of a CT imaging apparatus provided by a fourth embodiment of the present invention.

FIG. 11 is a structural schematic diagram of a CT imaging apparatus provided by a fourth embodiment of the present invention. As shown in FIG. 11, the CT imaging apparatus includes a rack 110, and may also include one or more X-ray transceiving components for the CT imaging apparatus as described above in the first embodiment, the second embodiment or the third embodiment, in which the above one or more X-ray transceiving components are installed on the rack 110.

Specifically, FIG. 11 shows a condition in which two X-ray transceiving components 500 are installed on the rack 110. In other conditions, the number of the X-ray transceiving components 500 may also be increased or decreased. The above X-ray transceiving components in FIGS. 1-4 may also be installed on the rack 110.

When performing CT imaging, a rotary rack 110 makes quadrate-tapered or fan-shaped X-ray beams emitted by a bulb device on the rotary rack 110 scan a scanned object, the corresponding detector device receives the X-ray beams and generates image signals, and the corresponding reconstruction method may be selected to reconstruct the received image signals according to position relationships of different X-ray transceiving components or different position relationships of the same X-ray transceiving components to obtain an image of the scanned object.

In the embodiment of the present invention, one or more bulb devices emit quadrate-tapered or fan-shaped X-ray beams passing through a scanning field of view, and a plurality of detector devices are employed to receive X-rays passing through different areas within the scanning field of view. Thereby, even if the one or more bulb devices have a smaller focus, a larger scanning field of view can still be formed such that a higher spatial resolution is provided, image quality is improved, and an application range is expanded while the scanning field of view is not sacrificed.

Figure 12:
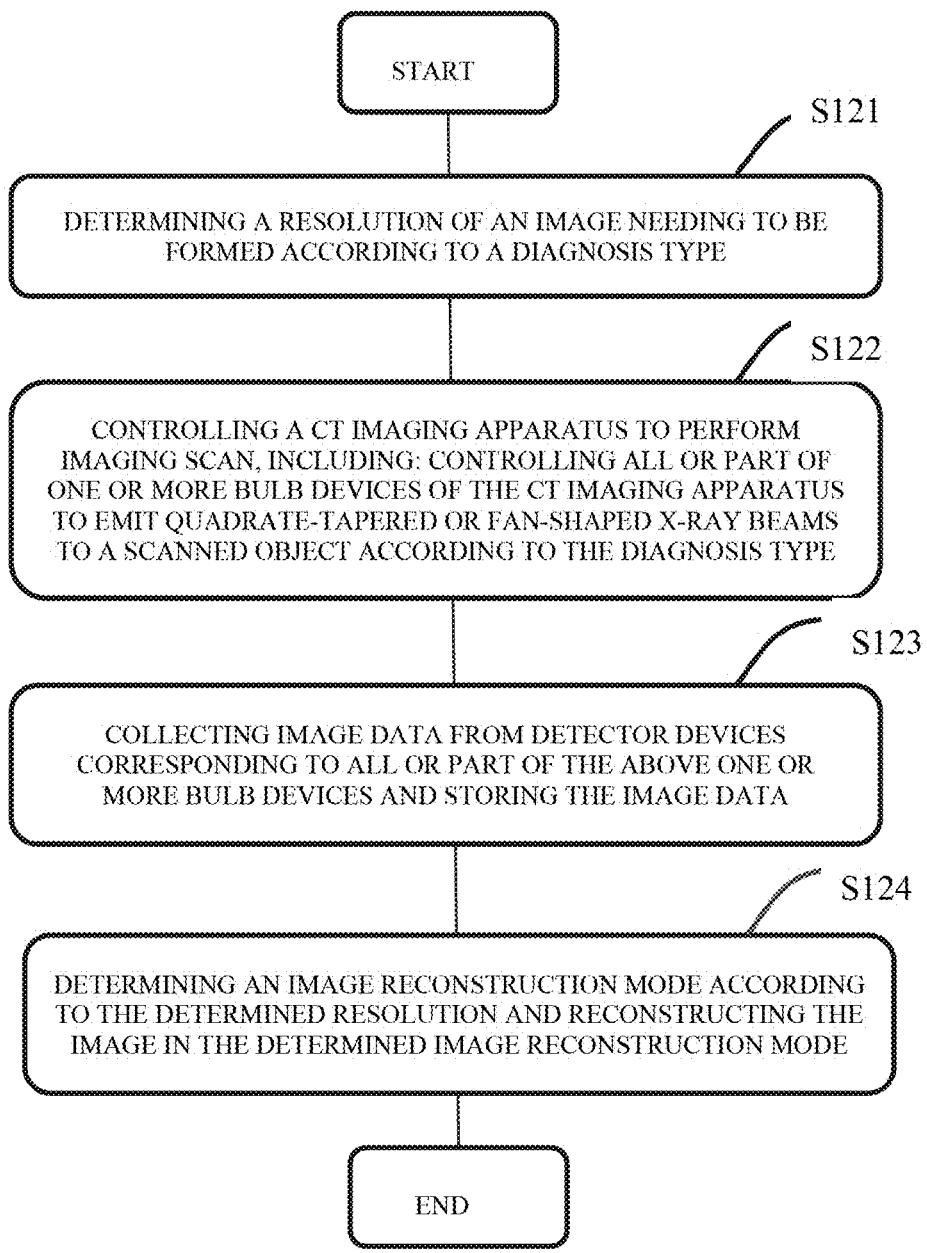
FIG. 12 is a flow chart of a CT imaging method provided by one embodiment of the present invention.

FIG. 12 is a flow chart of a CT imaging method provided by one embodiment of the present invention. As shown in FIG. 12, the CT imaging method of the embodiment of the present invention may include the following steps S121-S124.

Step 121: determining a resolution of an image needing to be formed according to a diagnosis type. The diagnosis type may include, e.g., whole-body scanning diagnosis, callback scanning diagnosis for a lesion area, and the like. However, since the above CT imaging apparatus of the present invention is utilized, a higher resolution can be achieved. For example, in an embodiment of the present invention, a plurality of levels of resolutions, e.g., 0.3 mm, 0.1 mm, 0.01 mm, 0.005 mm, and the like may be provided. When the whole-body scanning diagnosis is employed, a lower resolution, e.g., 0.3 mm or 0.1 mm, or the like may be selected; while when the callback scanning diagnosis for the lesion area is performed, a higher resolution, e.g., 0.01 mm or 0.005 mm may be selected according to the actual condition of the lesion.

Step S122: controlling a CT imaging apparatus to perform imaging scan, including: controlling all or part of one or more bulb devices of the CT imaging apparatus to emit quadrate-tapered or fan-shaped X-ray beams to a scanned object according to the diagnosis type. The above CT imaging apparatus may be the CT imaging apparatus described in the above embodiments of the present invention, which includes a plurality of detector devices corresponding to the above plurality of bulb devices and configured to receive the quadrate-tapered or fan-shaped X-ray beams emitted by the corresponding bulb devices, each quadrate-shaped or fan-shaped X-ray beam including X-rays passing through a scanning field of view, wherein the plurality of detector devices are configured to receive X-rays passing through different areas within the scanning field of view, the one or more bulb devices are micro-focus bulb devices, and the plurality of detector devices are flat panel detectors or photoelectric coupling detectors.

In Step S122, when the whole-body scanning diagnosis or other large-area scanning diagnosis is selected, all the bulb devices may be controlled to operate to emit the quadrate-tapered or fan-shaped X-ray beams into the corresponding detector devices. When the callback scanning diagnosis for the lesion area is selected, only the bulb devices corresponding to the lesion area may be allowed to operate and emit the quadrate-tapered or fan-shaped X-ray beams into the corresponding detector devices.

Step 123: collecting image data from detector devices corresponding to all or part of the above one or more bulb devices and storing the image data. Since the above CT imaging apparatus of the present invention employs micro-focus bulb devices and flat panel or photoelectric coupling detector devices, an image of a higher resolution can be obtained. It can be understood that, in the raw image data stored in Step S123, more data points (pixel points) are contained in a smaller data area.

Step S124: determining an image reconstruction mode according to the determined resolution and reconstructing the image in the determined image reconstruction mode. The above image reconstruction mode includes a first image reconstruction mode and a second image reconstruction mode.

Specifically, the first image reconstruction mode includes: dividing the stored image data into data blocks and reconstructing the image according to the data blocks, each data block including data obtained by fusing data of a plurality of pixel points. It can be understood that, in the first image reconstruction mode, in order to further improve a data processing speed and imaging efficiency in the case of ensuring that requirements for image quality are achieved, data of a plurality of smaller data points is fused and the fused data serves as one larger data point, such that an image of the corresponding quality can be quickly obtained by reconstructing the image according to data of all the larger data points. Obviously, in the case of, e.g., the whole-body scanning diagnosis or others in which requirements for a resolution are not high, there will be a higher imaging efficiency with the first image reconstruction mode.

The second image reconstruction mode includes: reconstructing the image according to data of all pixel points in the stored image data. It can be understood that in the second image reconstruction mode, in order to achieve a higher image quality, data points of the minimum unit serve as a basis of image reconstruction instead of data fusion, such that an image of a higher resolution can be obtained. Obviously, it may be in particular applied in the callback diagnosis for the lesion area.

Optionally, after the image is reconstructed with the first image reconstruction mode, the following steps may further be included:
  judging whether a contrast agent has been used for a scanned object;
  if it has, positioning a highlighted area in the reconstructed image;
  performing image reconstruction on the highlighted area with the second image reconstruction mode. Optionally, image reconstruction may also be performed on the highlighted area with the first image reconstruction mode, as long as areas of the divided data blocks are smaller (the data points contained are less and data accuracy is higher).

Figure 13:
FIG. 13 is an image obtained by performing contrast agent imaging by a CT imaging method of an embodiment of the present invention.

FIG. 13 is an image obtained by performing contrast agent imaging by a CT imaging method of an embodiment of the present invention. It can be seen from FIG. 13 that a higher spatial resolution can be realized and a scanning field of view of the traditional CT imaging apparatus can be achieved by the CT imaging method of the embodiment of the present invention. Unobvious pathological change can be diagnosed with the CT imaging apparatus of the embodiment of the present invention, i.e., pathological change is found at the early stage of a disease such that a patient can be timely treated. Moreover, by performing image reconstruction on the highlighted area in an image with the second image reconstruction mode, repetition of ray scanning on a scanned object is avoided. After the lesion area is found, a clearer image of the lesion area may be obtained only by changing the image reconstruction modes, so as to realize low-dose diagnosis.

Optionally, in Step S122, controlling the CT imaging apparatus to perform the imaging scan includes:
  performing integrated imaging on the scanned object by combining the above CT imaging apparatus with a single-photon emission computed tomography imaging apparatus or a positron emission tomography imaging apparatus to obtain an image of the scanned object;
  positioning a highlighted area in the obtained image of the scanned object;
  performing image reconstruction on the highlighted area with the second image reconstruction mode. Optionally, image reconstruction may also be performed on the highlighted area with the first image reconstruction mode, as long as areas of the divided data blocks are smaller (the data points contained are less and data accuracy is higher).

Figure 14:
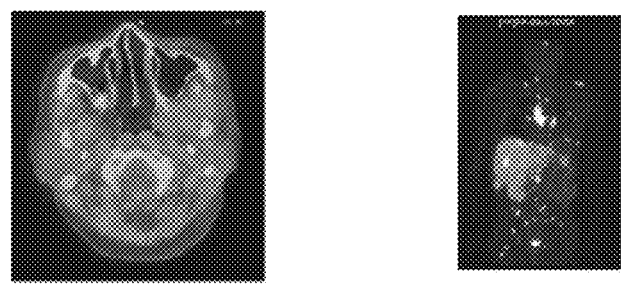
FIG. 14 is an image obtained by performing integrated imaging by a CT imaging apparatus of an embodiment of the present invention in combination with a single-photon emission computed tomography imaging apparatus or a positron emission tomography imaging apparatus and a highlighted area obtained by positioning in the image.

FIG. 14 is an image obtained by performing integrated imaging by a CT imaging apparatus of an embodiment of the present invention in combination with a single-photon emission computed tomography imaging apparatus or a positron emission tomography imaging apparatus and a highlighted area obtained by positioning in the image. It can be seen from FIG. 14 that by imaging with the CT imaging apparatus of the present invention in combination with the single-photon emission computed tomography imaging apparatus or the positron emission tomography imaging apparatus, a clear image with a highlighted area (that may be regarded as the lesion area) can be obtained.

When image reconstruction is performed on the highlighted area with the second image reconstruction mode, a clear image of the lesion area may just be obtained such that repetition of ray scanning on the scanned object is avoided and low-dose diagnosis is also realized.

Figure 15:
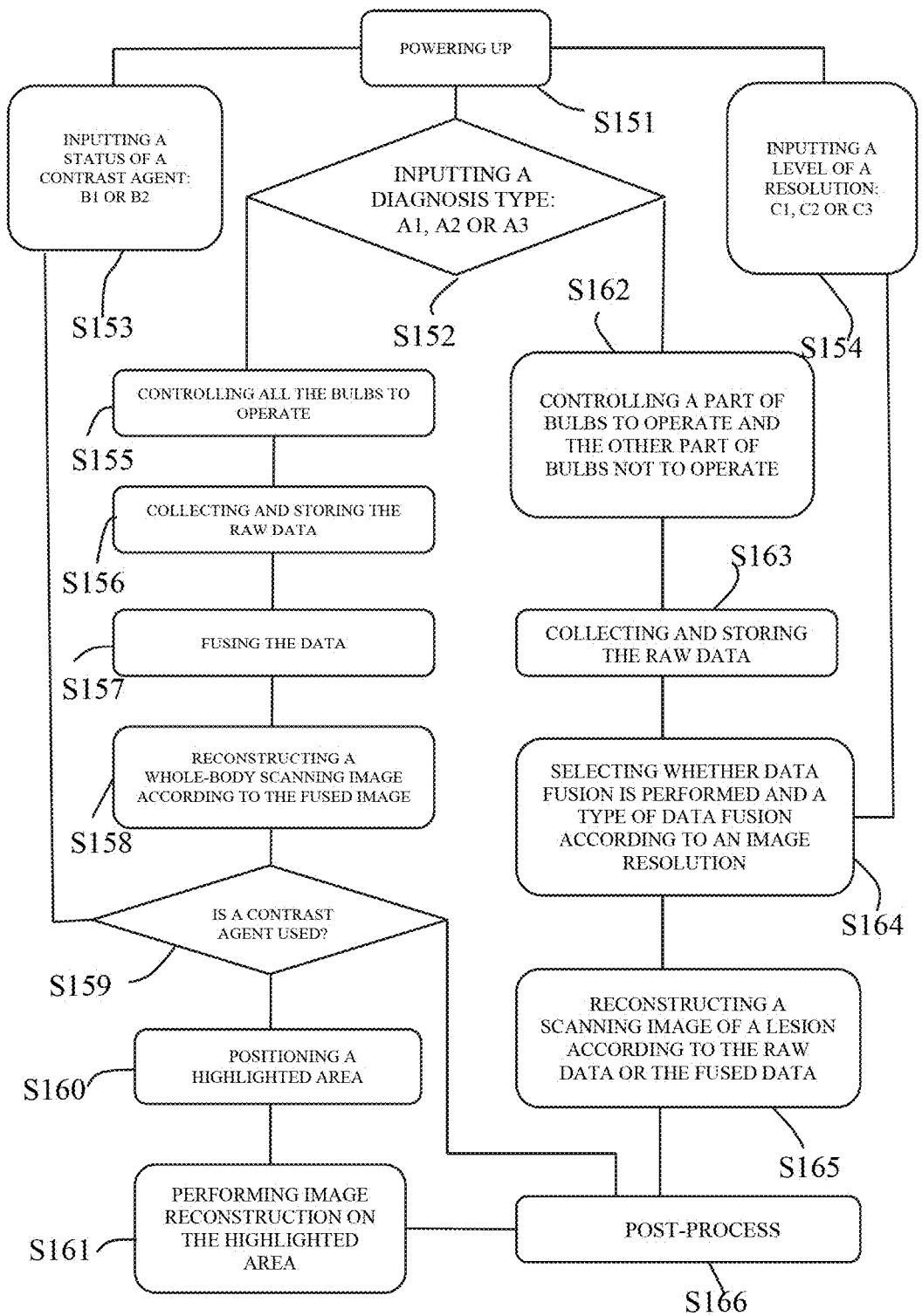
FIG. 15 is a flow chart of one exemplary application of a CT imaging method of an embodiment of the present invention.

FIG. 15 is a flow chart of one exemplary application of a CT imaging method of an embodiment of the present invention. As shown in FIG. 15, the exemplary application includes the following steps.

Step S151: powering up a CT imaging apparatus;

Step S152: inputting a diagnosis type, in which A1 is whole-body scanning diagnosis, A2 is larger-range scanning diagnosis, and A3 is callback scanning diagnosis for a lesion area;

Step S153: inputting a status of a contrast agent, in which B1 is that a contrast agent has been used and B2 is that no contrast agent has been used;

Step S154: inputting a level of an image resolution, in which C1 is a macro image, C2 is a meso image, and C3 is a micro image.

When A1 or A2 is selected in Step S152, Steps S155-S158, i.e., controlling all the bulbs to operate, storing the raw data collected from detectors, fusing the data, and reconstructing a whole-body scanning image according to the fused data, are performed.

After the whole-body scanning image is obtained, Steps S159-S161, i.e., judging whether a contrast agent has been used for the scanned object, positioning a highlighted area of the whole-body scanning image when it is determined that a contrast agent has been used, and performing image reconstruction on the highlighted area, are performed. A higher resolution, e.g., C3 may be selected to perform image reconstruction on the highlighted area, i.e., utilizing the second image reconstruction mode.

If the diagnosis type A3 is selected in Step S152, Steps S162-S165, i.e., controlling one part of bulbs to operate and the other part of bulbs not to operate, storing the raw data collected from detectors, selecting whether data fusion is performed and a type of data fusion according to an image resolution, and reconstructing a scanning image of a lesion according to the raw data or the fused data, are performed.

For example, when a macro scanning image of the lesion is needed, the corresponding data fusion type is selected to fuse data points in a larger area in Step S164; when a meso scanning image of the lesion is needed, the corresponding data fusion type is selected to fuse data points in a smaller area; and when a micro scanning image of the lesion is needed, it is selected that no data fusion is performed, but the scanning image of the lesion is reconstructed directly according to the raw data in Step S165.

In other words, the resolution corresponding to the first image reconstruction mode includes a plurality of levels. In the first image reconstruction mode, the number of data points in data blocks in which data is fused is different for different levels of resolution.

Step S166: performing post-process on the obtained image.

Some exemplary embodiments have been described in the above. However, it should be understood that various modifications may be made thereto. For example, if the described techniques are carried out in different orders, and/or if the components in the described system, architecture, apparatus or circuit are combined in different ways and/or replaced or supplemented by additional components or equivalents thereof, proper results may still be achieved. Accordingly, other implementation also falls within a protection range of the Claims.

What is claimed is:

1. An X-ray transceiving component for a CT imaging apparatus, comprising:
    a plurality of X-ray emitters configured to emit quadrate-tapered or fan-shaped X-ray beams;
    a plurality of detector devices configured to receive the quadrate-tapered or fan-shaped X-ray beams emitted by said plurality of X-ray emitters, the quadrate-tapered or fan-shaped X-ray beams comprising X-rays passing through a scanning field of view, wherein said plurality of detector devices are configured to receive X-rays passing through different areas within the scanning field of view, said plurality of X-ray emitters comprise micro-focus X-ray emitters, and said plurality of detector devices comprise flat panel detectors or photoelectric coupling detectors;
    wherein each X-ray emitter of said plurality of X-ray emitters corresponds to a respective detector device of said plurality of detector devices, and each detector device of said plurality of detector devices is configured to receive quadrate-tapered or fan-shaped X-ray beams emitted by a corresponding X-ray emitter of said plurality of X-ray emitters; and
    wherein said plurality of X-ray emitters and said plurality of detector devices are provided at intervals outside said scanning field of view, and each detector device of said plurality of detector devices is provided between two X-ray emitters of said plurality of X-ray emitters.

2. The X-ray transceiving component for a CT imaging apparatus according to claim 1, wherein a center of quadrate-tapered or fan-shaped X-ray beams emitted by at least one of said plurality of X-ray emitters deviates from a center of said scanning field of view, or centers of quadrate-tapered or fan-shaped X-ray beams emitted by said plurality of X-ray emitters all coincide with the center of said scanning field of view.

3. An X-ray transceiving component for a CT imaging apparatus, comprising:
    a plurality of X-ray emitters configured to emit quadrate-tapered or fan-shaped X-ray beams;
    a plurality of detector devices configured to receive the quadrate-tapered or fan-shaped X-ray beams emitted by said plurality of X-ray emitters, the quadrate-tapered or fan-shaped X-ray beams comprising X-rays passing through a scanning field of view, wherein said plurality of detector devices are configured to receive X-rays passing through different areas within the scanning field of view, said plurality of X-ray emitters comprise micro-focus X-ray emitters, and said plurality of detector devices comprise flat panel detectors or photoelectric coupling detectors, wherein said plurality of X-ray emitters correspond to said plurality of detector devices respectively and each detector device of said plurality of detector devices is configured to receive the quadrate-tapered or fan-shaped X-ray beams emitted by a corresponding X-ray emitter of said plurality of X-ray emitters, and wherein said plurality of detector devices comprises a first detector device, a second detector device, and a third detector device and said plurality of X-ray emitters comprises a first X-ray emitter, a second X-ray emitter, and a third X-ray emitter; and a first supporting member and a second supporting member;

said first supporting member comprises an upper supporting surface and a lower supporting surface, said first detector device is provided on said lower supporting surface of said first supporting member, said first X-ray emitter and said second X-ray emitter are separately provided at two sides of said upper supporting surface of said first supporting member;

said second supporting member comprises an upper supporting surface and a lower supporting surface, said third X-ray emitter is provided on said lower supporting surface of said second supporting member, said second detector device and said third detector device are separately provided at two sides of said upper supporting surface of said second supporting member;

said first detector device provided on said lower supporting surface of said first supporting member is opposite to said third X-ray emitter provided on said lower supporting surface of said second supporting member so as to be capable of receiving the quadrate-tapered or fan-shaped X-ray beams emitted by said third X-ray emitter provided on said lower supporting surface of said second supporting member; and said second detector device and said third detector device provided on said upper supporting surface of said second supporting member are respectively opposite to said first X-ray emitter and said second X-ray emitter provided on said upper supporting surface of said first supporting member so as to be capable of receiving the quadrate-tapered or fan-shaped X-ray beams emitted by said first X-ray emitter and said second X-ray emitter provided on said upper supporting surface of said first supporting member respectively.

4. The X-ray transceiving component for a CT imaging apparatus according to claim 3, wherein a center of the quadrate-tapered or fan-shaped X-ray beams emitted by said third X-ray emitter provided on said lower supporting surface of said second supporting member coincides with a center of said scanning field of view or deviates from the center of said scanning field of view.

5. A CT imaging method, comprising the steps of:
determining a resolution of an image needing to be formed according to a diagnosis type;
controlling a CT imaging apparatus to perform imaging scan, comprising: controlling all or part of a plurality of X-ray emitters of the CT imaging apparatus to emit quadrate-tapered or fan-shaped X-ray beams to a scanned object according to said diagnosis type, said CT imaging apparatus further comprising a plurality of detector devices, said plurality of detector devices corresponding to said plurality of X-ray emitters and being configured to receive the quadrate-tapered or fan-shaped X-ray beams emitted by corresponding X-ray emitters of said plurality of X-ray emitters, each quadrate-shaped or fan-shaped X-ray beam comprising X-rays passing through a scanning field of view, wherein said plurality of detector devices are configured to receive X-rays passing through different areas within the scanning field of view, said plurality of X-ray emitters comprise micro-focus X-ray emitters, and said plurality of detector devices comprise flat panel detectors or photoelectric coupling detectors;

collecting image data from said plurality of detector devices corresponding to all or part of said plurality of X-ray emitters and storing said image data; and determining an image reconstruction mode according to the determined resolution and reconstructing an image in the determined image reconstruction mode, said image reconstruction mode comprising a first image reconstruction mode and a second image reconstruction mode; said first image reconstruction mode comprising: dividing the stored image data into data blocks and reconstructing the image according to said data blocks, each data block comprising data obtained by fusing data of a plurality of pixel points; said second image reconstruction mode comprising: reconstructing the image according to data of all pixel points in the stored image data.

6. The CT imaging method according to claim 5, further comprising reconstructing the image with the first image reconstruction mode, wherein the reconstructing the image with the first image reconstruction comprises the steps of:
judging whether a contrast agent has been used for a scanned object;
if a contrast agent has been used, positioning a highlighted area in the reconstructed image; and
performing image reconstruction on said highlighted area with said first image reconstruction mode or said second image reconstruction mode.

7. The CT imaging method according to claim 5, further comprising the steps of:
performing integrated imaging on said scanned object by combining said CT imaging apparatus with a single-photon emission computed tomography imaging apparatus or a positron emission tomography imaging apparatus to obtain an image of said scanned object;
positioning a highlighted area in the obtained image of the scanned object; and
performing image reconstruction on said highlighted area with said first image reconstruction mode or said second image reconstruction mode.

8. The CT imaging method according to claim 5, wherein a resolution corresponding to said first image reconstruction mode comprises a plurality of levels, and in the first image reconstruction mode, a number of data points in said data blocks is different for different levels of resolution.

* * * * *